United States Patent [19] [11] 3,993,807
Stabenow et al. [45] Nov. 23, 1976

[54] ACTIVATION OF SUBSTRATES FOR ELECTROLESS METALLIZATION WITH ZERO VALENT PALLADIUM COMPLEX

[75] Inventors: Joachim Stabenow, Weinheim; Gerd Wunsch, Speyer; Paul Deigner, Weisenheim; Franz-Josef Mueller, Limburgerhof; Werner Loeser, Ludwigshafen; Werner Steck, Mutterstadt, all of Germany

[73] Assignee: BASF Aktiengesellschaft, Ludwigshafen, Rhine, Germany

[22] Filed: Oct. 24, 1975

[21] Appl. No.: 625,657

[30] Foreign Application Priority Data
Oct. 29, 1974    Germany.............................. 2451217

[52] U.S. Cl. .................................. 427/229; 106/1; 427/304; 427/305; 427/306; 427/328
[51] Int. Cl.² ....................... C23C 3/02; B05D 3/02
[58] Field of Search ........... 427/304, 305, 306, 229, 427/328; 106/1; 260/429 J

[56]       References Cited
           UNITED STATES PATENTS
3,438,805    4/1969    Potrafke ............................ 427/304

| | | |
|---|---|---|
| 3,501,332 | 3/1970 | Buckman ............................ 427/304 |
| 3,592,680 | 7/1971 | Bayer ................................. 427/304 |
| 3,622,367 | 11/1971 | Haag et al. .......................... 427/304 |
| 3,622,607 | 11/1971 | Fenton ............................. 260/429 J |
| 3,684,534 | 8/1972 | Emerson ................................. 106/1 |
| 3,937,857 | 2/1976 | Brummett et al. ................... 427/229 |

*Primary Examiner*—Ralph S. Kendall
*Assistant Examiner*—John D. Smith
*Attorney, Agent, or Firm*—Johnston, Keil, Thompson & Shurtleff

[57]             ABSTRACT

A process for metallizing substrates by activation of the substrate by deposition of palladium from a palladium complex, followed by electroless metallization. The palladium is deposited on the substrate by dipping the substrate into a solution of a palladium(O) complex and decomposing this complex at from 100° to 300° C.

With this method it is possible to effectively activate substrates which are attacked by acid or alkali or swollen by organic solvents.

10 Claims, No Drawings

ACTIVATION OF SUBSTRATES FOR ELECTROLESS METALLIZATION WITH ZERO VALENT PALLADIUM COMPLEX

BACKGROUND OF THE INVENTION

The present invention relates to a simple process for metallizing substrates by effective activation of the substrate by deposition of palladium from a palladium compound, followed by electroless metallization of the activated substrate in a metallizing bath.

As disclosed, e.g., in the monograph by F. A. Loewenheim, Metal Coating of Plastics, Noyes Data Corp., Park Ridge, N.J., 1970, the pretreatment of substrates for electroless metallization is usually very time-consuming. After a chemical pretreatment, e.g. with chromosulfuric acid, or a mechanical pretreatment of the substrate surfaces, the conventional activation entails sensitizing the substrate with tin salts, rinsing it and then applying palladium chloride to activate the substrate.

U.S. Pat. No. 3,501,332 discloses the activation of plastics with zero-valent metal complexes, e.g. bis-(cyclooctadienyl)-nickel in organic solvents. In this method, the combination of metal complex and organic solvent is intended to swell the surface of the substrate so as to permit the metal complex to penetrate to a depth of at least 5 $\mu$ and preferably to a depth of from 5 to 80 $\mu$. Substrates whose surface is difficult to swell must be subjected to a special pretreatment.

THE INVENTION

It is an object of the present invention to provide an effective method of activating substrates with palladium for electroless metallization, which is applicable even to substrates which are insoluble in the solvents employed, can be carried out in one step and in a simple manner, even at elevated temperatures, is also applicable to substrates which are attacked by acid and alkali, and effectively contributes toward the formation of a smooth surface after metallizing, even on substrates which are not entirely smooth, such as anodized aluminum sheet. It is a further object of the invention to provide activation baths which remain stable in use over a long period.

We have found that these objects are achieved and that the desired advantages may be attained by a method of plating a substrate which comprises contacting the surface of the substrate with a solution of a zero-valent palladium complex in an organic solvent, the ligands of said complex being selected from the group consisting of a. an unsaturated ketone of the formula

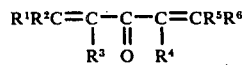

wherein $R^1$, $R^3$, $R^4$ and $R^6$ are hydrogen or alkyl of 1 to 5 carbon atoms and $R^2$ and $R^5$ are alkyl of 1 to 5 carbon atoms or aryl or cycloalkyl of 6 to 11 carbon atoms, and b. a phosphite of the formula

wherein R is alkyl or aryl, together with an olefinically or acetylenically unsaturated organic compound of 3 to 16 carbon atoms, decomposing the said complex on the substrate at from 100° to 300° C and depositing a metal coating on the so-treated substrate by contacting said substrate with an electroless chemical plating bath.

The process is preferably carried out with solutions of the complexes in benzene, especially in an alkyl-substituted benzene, e.g. ethylbenzene, xylene or, preferably, toluene.

Preferred palladium(O) complexes with unsaturated ketones of the formula A are the complexes or systems of palladium(O) with dibenzalacetone

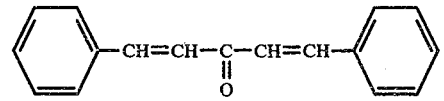

which not only exhibit a good activating action but also particularly high stability in solution in the above solvents. Though the palladium(O) complexes, e.g. the palladium(O) dibenzalacetone complex, are frequently represented in a simplified form as Pd(dba)$_2$, the complexes contain one or more palladium atoms, depending on the conditions under which they are synthesized, and it would therefore be better to refer to them as palladium(O)-ligand systems.

Examples of phosphite compounds are the trialkyl phosphites in which each alkyl is of 1 to 5 carbon atoms, and, preferably, the triaryl phosphites in which each aryl is of 6 to 10 carbon atoms, and especially triphenyl phosphite.

Particularly suitable olefinically unsaturated $\pi$-acceptors are the esters and above all the alkyl esters of maleic acid or fumaric acid, and preferably, maleic anhydride. Very suitable esters of this type are dimethyl maleate and dimethyl fumarate. Acrylonitrile and olefinically unsaturated monomers with e-values greater than 1.2 (cf. "Polymer Handbook," Interscience Publ., New York, 1966, page II-341) may also be used.

Examples of suitable acetylenically unsaturated organic compounds of 6 to 16 carbon atoms which act as $\pi$-acceptors and ligands in the palladium(O) complexes alongside the above phosphite ligands are the acetylenically unsaturated hydrocarbons and compounds in which the acidic groups have been replaced for example by COO-alkyl or CO-alkyl groups, in particular 1,4-butynediol and 1,4-butynediol dialkyl ethers, e.g. 1,4-butynediol dimethyl ether.

The preferred palladium(O) complexes are those which contain maleic anhydride and triphenyl phosphite, or dimethyl maleate and triphenyl phosphite, as ligands, and especially the palladium(O) dibenzalacetone complexes, which have proved particularly suitable.

The palladium(O) complexes with unsaturated ketones A may be manufactured in the manner described in Example 1. The mixed palladium(O) phosphite complexes which contain olefinically or acetylenically unsaturated compounds are preferably manufactured by adding the phosphite to the palladium(O) dibenzalacetone complex and then adding the olefinically or acetylenically unsaturated compound, e.g. maleic anhydride or 1,4-butynediol dimethyl ether, or by adding the olefinically or acetylenically unsaturated compound to the palladium(O) dibenzalacetone complex and then adding the phosphite.

We have found, surprisingly, that the stability of the solutions of the said palladium(O) complexes may be increased by using benzene and, in particular, alkylated benzenes, e.g. toluene, as the solvent. The concentrations of the complexes in the solutions are from about 15 mg/l to the saturation concentration at room temperature, and preferably from about 50 mg/l to about 2 g/l, depending on the nature of the complex and of the solvent. Although halohydrocarbons and e.g. acetonitrile, tetrahydrofuran or dimethylformamide are less suitable solvents because they may slightly decompose the metal complexes, this decomposing effect may be used to activate the substrate. We have found it possible, after dipping a substrate into a solution of palladium dibenzalacetone complex in toluene at room temperature and then dipping the treated substrate into a chlorinated hydrocarbon, e.g. dichloroethylene, trichloroethylene or tetrachloroethylene, at room temperature, to electrolessly plate the substrate, for example, in a cobalt salt bath. The complexes which are preferentially used are only slightly soluble in solvents, e.g. ethanol, metanol or cyclohexane.

Further, we have found that the stability of the palladium(O) complex solution used for activation may be further increased by admixture of further potential complex-forming agents, e.g. bis-(1-pyrazolyl)-2-methane and, especially, azobenzene.

A wide variety of substrates, e.g. metal substrates, oxidized metal substrates and substrates made of plastics materials including crosslinked plastics, are amenable to the activation according to the invention. We have found, as shown by electron microphotographs, that in the process of the invention swelling of the surface of the substrate is not necessary for activation since the nucleation centers are formed directly on the substrate surfaces, e.g. as palladium nuclei of from about 50 to 100 A in size, or as substantially coherent palladium films. This is particularly clear in the preferred method of activation, where the substrates, heated to from about 100° to 300° C, and especially from 130° to 250° C, are dipped into the palladium(O) complex solutions. It is surprising that, e.g., the palladium(O)-dibenzalacetone complex solutions are not only distinguished by good stability in air but, though they are themselves heat-labile, remain stable, in the form of solutions in toluene, even after being used practically daily for 2 months, and showed no appreciable decomposition of the complex, though the substrates were always at from about 200° to 250° C when dipped into the solutions at room temperature. The system

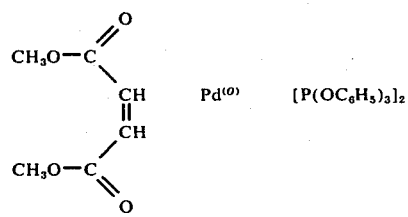

in toluene proved almost equally stable. Preferably, the heated substrate is dipped into the palladium(O) complex solutions (which are kept at room temperature) under an inert gas, e.g. under nitrogen, carbon dioxide or rare gases. Though a single dip of the hot substrate into the palladium(O) complex solutions is in most cases sufficient, such dipping can of course also be carried out several times, e.g. from 2 to 4 times. The number of dips (activations) is above all determined by the temperature employed, the heat storage capacity of the substrate, the nature and concentration of the complex and the nature of the additives in the solution. Preferably, the substrates are briefly grounded because of the risk of their becoming electrostatically charged.

In a suitable apparatus for the activation treatment, the container for the activating bath is provided with a slit-shaped orifice through which the heated substrates can briefly be introduced into the palladium(O) complex solution in the container. If the substrates are dipped in rapid succession, the container may be equipped with cooling means which keep the solution at about room temperature or below about 50° C.

To prevent the complex solutions from leaving streaks on the surface of the substrate when it is removed from the activating bath, which streaks may remain visible after metallizing, it has proved advantageous to rinse the substrates with a solvent, preferably with the same solvent as is used in the complex solution, after the dipping treatment.

Of course it is also possible to effect the activation according to the invention by dipping the substrates at about room temperature, one or more times, into the palladium(O) complex solutions (at about room temperature) and heating the treated substrates between dips, or after dipping.

The process is particularly suitable for the activation of cross-linked plastics substrates which are non-swellable and insoluble, for which substrates no special pretreatment is necessary, and for chemically sensitive substrates, such as substrates attacked by acid and alkali, e.g. certain metal substrates, such as aluminum substrates, the surfaces of which may also be anodized. With such substrates, surprisingly, the activation process of the invention levels out the resulting metallized surfaces to a certain extent, i.e. makes them smoother.

Prior to the activation according to the invention, it is advisable to clean the substrates, e.g., to rinse them with the solvent which is also used in the palladium(O) complex solution.

Conventional metallizing baths and conventional methods may be employed for the electroless metallization; these are described, e.g., in the monograph by W. Goldie, Metallic Coating of Plactics, Vol. I, Electrochemical Publications Ltd., Hatch End, Middlesex, England, 1968, especially in Chapter 9, in the previously cited monograph by F. A. Loewenheim, and especially by A. Brenner and G. E. Riddell, J. Res. Natl. Bur. Std., 37 (1), 31 (1946) and Proc. Amer. Electroplaters Society, 34 (1947), 156, and in U.S. Pat. Nos. 2,532,283 and 2,532,284.

The activation process has proved particularly advantageous when used in connection with the deposition of magnetic metal films, e.g. layers of cobalt, cobalt-phosphorus alloys or cobalt-nickel alloys. The thickness of the electroless films may be varied by conventional methods and is preferably from 0.05 to 1 $\mu$.

EXEMPLARY EMBODIMENTS

In the following Examples parts and percentages are by weight, unless stated otherwise. Parts by volume bear the same relation to parts by weight as the liter to the kilogram.

EXAMPLE 1

Preparation of a palladium(O)-dibenzalacetone complex 15 parts of $PdCl_2$ (59.75% Pd) in a solution of 10.7 parts of sodium chloride in 65 parts by volume of water, are heated to the boil, with thorough stirring, until all the $PdCl_2$ has dissolved. The water is then distilled off. The residue is taken up in 200 parts by volume of methanol. The solution is heated to 60° C, 61.5 parts of dibenzalacetone, 42.8 parts of $CH_3COONa.3H_2O$ and 175 parts of methanol are added, and the mixture is kept at 60° C for a further 5 minutes. The batch is then allowed to cool. A precipitate forms, which is filtered off under argon, and is washed 3 times with water, each time with about 100 parts by volume, and twice with methanol, each time with about 50 parts by volume. The product is dried under reduced pressure at room temperature. The red-violet crystals are readily soluble in aromatic hydrocarbons, e.g. benzene, toluene and other alkyl-aromatics.

Analysis: 70.8%, C, 5.3%, H, 6.3%, O, 17.4%, Pd, <0.5%, $Cl^-$.

This compound will be hereinafter referred to as the Pd-dba complex.

EXAMPLE 2

Preparation of a palladium(O)/bis-(triphenylphosphite)/maleic anhydride complex 3.6 parts of triphenyl phosphite are added to a solution of 2.9 parts of the Pd-dba complex of Examle 1 in 50 parts by volume of acetone under argon, whilst stirring thoroughly, whereupon the color of the solution changes, in the course of approximately a half-hour period starting from the addition, from a reddish brown to a dark yellowish green. 0.5 part of maleic anhydride is then added and stirring is continued for 2 hours at room temperature. The batch is then filtered to remove traces of a black precipitate and the filtrate is concentrated under reduced pressure until grey-green crystals separate out, which are purified by dissolving in ether and reprecipitating with ligroin.

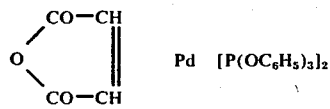

Light yellow crystals of melting point 135° – 137° C.

Analysis ($C_{40}H_{32}O_9P_2$. Pd): calculated: 58.2%, C; 4.0%, H; 7.5%, P; 12.9%, Pd. found: 58.4%, C; 3.9%, H; 7.5%, P; 12.8%, Pd.

EXAMPLE 3

Preparation of a palladium(O)/dimethyl maleate/triphenylphosphite complex 3.6 parts of a triphenylphosphite are added to a solution of 2.9 parts of the Pd-dba complex in 50 parts by volume of acetone, with thorough stirring, whereupon the color of the batch changes from a reddish brown to a dark yellowish green. 0.8 part of dimethyl maleate is added to the homogeneous solution and the batch is stirred for 2 hours at room temperature and then filtered under argon to remove traces of a black precipitate. The filtrate is concentrated under reduced pressure to give a mixture of an oil and brown crystals. The residue is taken up in 50 parts by volume of ether, the ether solution is filtered to remove insoluble matter and the filtrate is concentrated until crystallization starts; the crystallization can be intensified by adding 10 parts by volume of methanol. 1.3 g of a lemon-colored substance are obtained.

Elementary analysis: 71.6%, C; 5.3%, H; 12.5%, O; 5.1%, P, 5.2%, Pd.

The complex is readily soluble in alkyl-aromatics and in benzene.

EXAMPLE 4

Preparation of a palladium(O)/1,4-butynediol dimethyl ether/triphenylphosphite complex The procedure followed is as in Example 3 except that in place of 0.8 part of dimethyl maleate, 1.4 parts of 1,4-butynediol dimethyl ether is added to the reaction mixture of the Pd-dba complex and triphenylphosphite. Lemon-colored crystals are obtained, which are readily soluble in benzene and alkyl-aromatics and give stable solutions.

EXAMPLES 5 to 8

Solutions of further palladium(O) complexes were prepared by adding, in each case, 1.2 parts of triphenylphosphite to solutions of 0.58 part of the Pd-dba complex in 500 parts by volume of toluene, and then adding the following:

Example 5 : 0.13 part of acrylonitrile
Example 6 : 0.3 part of acrylamde
Example 7 : 0.4 part of vinyl propionate
Example 8 : 0.7 part of azobenzene Homogeneous palladium(O) complex solutions are obtained.

EXAMPLE 9

An anodized aluminum sheet is heated to 200° C and is dipped in this state for 5 seconds into a solution of the palladium(O)/1,4-butynediol dimethyl ether/bis-(triphenylphosphite) complex prepared according to Example 4, in toluene (1 g/l). This procedure is then repeated once more. Thereafter, a cobalt layer is deposited on the activated substrate in a conventional metallizing bath which contains cobalt ions, hypophosphite ions, citrate as complexing agent and ammonia and ammonium chloride to adjust the pH. A glossy, firmly adhering metal film is obtained.

EXAMPLE 10

A 70 μ thick polyethylene terephthalate film pretreated with sodium hydroxide solution is dipped for 5 minutes at room temperature into a solution of the palladium(O)/bis-(triphenylphosphite)/maleic anhydride complex prepared according to Example 2, in benzene (0.5 g/l); the activated plastics film is then taken out, dried and heated at 150° C for 12 minutes. After cooling to room temperature, the activated substrate is electrolessly plated with a layer of cobalt metal, as described in Example 9.

EXAMPLE 11

An aluminum sheet to which there has been bonded a 50 μ thick poly(amide-imide) film is heated to 240° C and rapidly dipped into a solution of the palladium-(O)/dimethyl maleate/triphenylphosphite complex prepared according to Example 3, in a xylene isomer mixture (0.4 g/l). This procedure is repeated twice more. Electroless plating in a cobalt bath, carried out as described in Example 9, produces a firmly adhering metal film.

EXAMPLE 12

An aluminum sheet provided with a firmly adhering, thin, heatcured layer of a dispersion of finely divided $\alpha$-$Fe_2O_3$ particles in a binder based on an epoxy resin is heated to 220° C and immediately dipped into a solution of 250 mg/l of the Pd-dba complex prepared according to Example 1, in ethyl benzene; when the temperatures have equalized, the substrate is taken out. The activated substrate which has cooled to room temperature is provided with a cobalt layer in a metallizing bath, as described in Example 9. A firmly adhering glossy metal layer is produced.

EXAMPLE 13

The procedure followed is as in Example 12 except that the aluminum sheet provided with the layer of dispersion is activated by heating it to 240° C, dipping it into a palladium complex solution which contains 5.8 g of the Pd-dba complex, 12 g of triphenylphosphite and 7 g of azobenzene per 5 liters of toluene, taking it out after 30 seconds and drying it in air. This procedure is repeated three more times. The substrate which has cooled is provided with a firmly adhering glossy metal layer in a metallizing bath, as described in Example 9.

We claim:

1. A method of plating a substrate which comprises contacting the surface of the substrate with a solution of a zero-valent palladium complex in an organic solvent, the ligands of said complex being selected from the group consisting of a. an unsaturated ketone of the formula $$R^1R^2C=C-C-C=CR^5R^6$$
$$\phantom{R^1R^2C=C}|\phantom{-}||\phantom{-}|$$
$$\phantom{R^1R^2C=C}R^3\phantom{-}O\phantom{-}R^4$$

wherein $R^1$, $R^3$, $R^4$ and $R^6$ are hydrogen or alkyl of 1 to 5 carbon atoms and $R^2$ and $R^5$ are alkyl of 1 to 5 carbon atoms or aryl or cycloalkyl of 6 to 11 carbon atoms, and b. a phosphite of the formula $$P(OR)_3$$

wherein R is alkyl or aryl, together with an olefinically or acetylenically unsaturated organic compound of 3 to 16 carbon atoms which are $\pi$-acceptors in the case of said olefinically unsaturated compounds and which act as $\pi$-acceptors and ligands in the palladium (O) complexes in the case of said acetylenically unsaturated compounds, decomposing the said complex on the substrate at from 100° to 300° C and depositing a metal coating on the so-treated substrate by contacting said substrate with an electroless chemical plating bath.

2. A method as claimed in claim 1, wherein the substrate consists essentially of aluminum.

3. A method as claimed in claim 1, wherein at least the surface of the substrate consists essentially of an organic polymer composition which does not dissolve or swell in the organic solvent of said complex, and said organic solvent is benzene or an alkyl-substituted benzene.

4. A method as claimed in claim 1, wherein the ligands of said zero-valent palladium complex are dibenzalacetone.

5. A method as claimed in claim 1, wherein the ligands of said zero-valent palladium complex are triphenylphosphite and an ester of a carboxylic acid selected from the group consisting of maleic acid and fumaric acid.

6. A method as claimed in claim 1, wherein further complexing agents for zero-valent palladium are added to the solution of the said zero-valent palladium complex.

7. A method of plating a substrate which comprises contacting the surface of the substrate, heated to from 100° to 300° C, with a solution of a zero-valent palladium complex in an organic solvent, the ligands of said complex being selected from the group consisting of a. unsaturated ketone of the formula $$R^1R^2C=C-C-C=CR^5R^6$$
$$\phantom{R^1R^2C=C}|\phantom{-}||\phantom{-}|$$
$$\phantom{R^1R^2C=C}R^3\phantom{-}O\phantom{-}R^4$$

wherein $R^1$, $R^3$, $R^4$ and $R^6$ are hydrogen or alkyl of 1 to 5 carbon atoms and $R^2$ and $R^5$ are alkyl of 1 to 5 carbon atoms or aryl or cycloalkyl of 6 to 11 carbon atoms, and b. a phosphite of the formula $$P(OR)_3$$

wherein R is alkyl or aryl, together with an olefinically or acetylenically unsaturated organic compound of 3 to 16 carbon atoms which are $\pi$-acceptors in the case of said olefinically unsaturated compounds and which act as $\pi$-acceptors and ligands in the palladium (O) complexes in the case of said acetylenically unsaturated compounds, and depositing a metal coating on the so-treated substrate by contacting said substrate with an electroless chemical plating bath.

8. A method as claimed in claim 7 wherein said olefinically or acetylenically unsaturated compound is maleic anhydride, an alkyl ester of maleic acid or fumaric acid, acrylonitrile, an acetylenically unsaturated hydrocarbon having 3 to 16 carbon atoms, 1,4-butynediol or a 1,4-butynediol dialkyl ether.

9. A method as claimed in claim 1 wherein said olefinically or acetylenically unsaturated compound is maleic anhydride, an alkyl ester of maleic acid or fumaric acid, acrylonitrile, an acetylenically unsaturated hydrocarbon having 3 to 16 carbon atoms, 1,4-butynediol or a 1,4-butynediol dialkyl ether.

10. A method as claimed in claim 1 wherein said unsaturated organic compound of 3 to 16 carbon atoms is an olefinically unsaturated monomer with an $e$-value greater than 1.2.

* * * * *